United States Patent [19]

Fischer et al.

[11] Patent Number: 5,173,426
[45] Date of Patent: Dec. 22, 1992

[54] DNAS ENCODING GENETICALLY ENGINEERED LOW OXYGEN AFFINITY MUTANTS OF HUMAN HEMOGLOBIN

[75] Inventors: James J. Fischer, Guilford; Susan J. Baserga, New Haven, both of Conn.

[73] Assignee: Yale University, New Haven, Conn.

[21] Appl. No.: 417,949

[22] Filed: Oct. 6, 1989

[51] Int. Cl.$^5$ .................. C12N 15/70; C12N 15/74; C12N 15/12
[52] U.S. Cl. .................. 435/252.3; 435/69.6; 435/172.3; 435/320.1; 536/27
[58] Field of Search .................. 435/69.6, 172.3, 252.3, 435/320.1; 514/6; 536/27

[56] References Cited

U.S. PATENT DOCUMENTS 5,028,588  7/1991  Hoffman .................. 514/6

FOREIGN PATENT DOCUMENTS 1534  1/1988  PCT Int'l Appl.

OTHER PUBLICATIONS

Suggs et al. PNAS 78: 6613 (1981).
Fioretti et al. Biochem. Biophy. Res Comm 68:1169 (1976).
Barra et al. FEBS Lett. 64:76 (1976).
Dickerson, Hemoglobin: Structure, function, evolution, & pathology. Benjamin/Cummings pubs. Calif. 1983.

Primary Examiner—Richard A. Schwartz
Assistant Examiner—J. LeGuyader
Attorney, Agent, or Firm—Frishauf, Holtz, Goodman & Woodward

[57] ABSTRACT

A substantially pure polynucleotide coding for an alpha and/or beta human globin, the globin when part of a hemoglobin molecule confering lower oxygen affinity than normal hemoglobin to result in a mutant hemoglobin, the mutant hemoglobin having an oxygen affinity measured for stripped hemoglobin characterized by a $P_{50}$ of 30 torr to 3 atmospheres and/or by a Hill coefficient between 2.5 and 1.0. Such mutant hemoglobin being useful to increase tissue oxygenation in a patient, to replace hemoglobin in the bloodstream of a patient and to treat patients suffering from burns.

17 Claims, 3 Drawing Sheets

DNAS ENCODING GENETICALLY ENGINEERED LOW OXYGEN AFFINITY MUTANTS OF HUMAN HEMOGLOBIN

BACKGROUND OF THE INVENTION

1. Field of the Invention

The present invention concerns genetically engineered low oxygen affinity mutants of human hemoglobin and the use of the same to increase tissue oxygenation in a human patient or to replace hemoglobin in a human patient. One aspect of the present invention resides in providing more oxygen to tumors.

2. Background Information

Blood consists of plasma and cells floating within it. The cells comprise white blood cells (leukocytes), platelets and red blood cells (erythrocytes). Red blood cells contain a protein, hemoglobin, which imparts color. It is the hemoglobin (Hb) which is involved in the transport of oxygen and carbon dioxide and which plays a role in regulating blood pH.

Each molecule of hemoglobin comprises four smaller subunits, called polypeptide chains. These are the protein or globin parts of hemoglobin. A heme group, which is an iron-protoporphyrin complex, is associated with each polypeptide subunit and is responsible for the reversible binding of one molecule of oxygen. Normal adult hemoglobin is made up of two different kinds of polypeptide subunits. One is called the alpha chain containing 141 amino acid residues and the other is called the beta chain and contains 146 amino acid residues. Two of each kind of such polypeptide chains are arranged in the form of a truncated tetrahedron which has an overall shape of an ellipsoid.

There are almost 300 known mutations of hemoglobin. Mutations lead to changes in the amino acid structure of the polypeptide chains. The abnormal gene responsible for sickle-cell anemia causes the normal glutamic amino acid residue at position six of the beta chain to be substituted by a valine group. Few of the known hemoglobin mutants, however, cause disease. Most mutants contain a mixture of mutant and normal hemoglobin.

The reversible combination of hemoglobin and oxygen is represented by the following reaction:

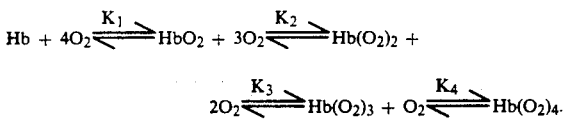

The equilibrium constants for each step are not the same because an oxygen molecule on one heme group changes (increases) the affinity of the other hemes for additional oxygen molecules. This alteration in binding affinity during oxygenation is called heme-heme interaction or cooperativity. Because of this cooperativity, the relationship between the partial pressure of oxygen and the amount of oxygen bound to hemoglobin is represented by a sigmoid curve. It is customary to characterize this sigmoid curve by two parameters: $P_{50}$, the partial pressure of oxygen at which half saturation of the hemoglobin takes place; and n, the so-called Hill coefficient, which is a measure of cooperativity and thus the sigmoid shape of the curve. The Hill coefficient can vary in value from 1.0, corresponding to a lack of cooperativity and a straight line relationship, to 4.0, maximum cooperativity and an extreme sigmoid shape.

The oxygen affinity of hemoglobin is influenced by multiple factors including pH and the presence of certain inorganic phosphate molecules, most importantly 2,3-diphosphoglycerate. The term stripped hemoglobin is used to refer to hemoglobin free of these modulating inorganic phosphates. Stripped normal human hemoglobin has a $P_{50}$ value of approximately 10 torr and a Hill coefficient of 2.8 to 3.0. The decrease in oxygen affinity with decrease in pH (more acidic) is known as the Bohr effect. An extreme form of the Bohr effect, known as the Root effect is observed for certain fish hemoglobin for which the value of $P_{50}$ at pH circa 6.5 may be as high as several atmospheres.

X-irradiation is an important modality in the treatment of solid tumors. Two-thirds of the biological damage produced by x-rays occurs indirectly and is mediated by the action of free radicals. Oxygen combines with the free radicals and "fixes" the lesion in the cell. Therefore a thoroughly oxygenated tumor will be more responsive to x-irradiation.

Most solid tumors are not uniformly oxygenated. About 10-20% of the cells in experimental tumors are hypoxic. This occurs, at least in part, because tumors outgrow their blood supply. If more oxygen could be delivered to a tumor, cell death would be greater and tumor curability would improve.

SUMMARY OF THE INVENTION

It is an object of the present invention to provide genetically engineered low oxygen affinity mutants of human hemoglobin.

It is another object of the invention to provide a method of increasing tissue oxygenation in a human patient.

It is a further object of the invention to provide a method of replacing hemoglobin in the bloodstream of a human patient.

It is also an object of the present invention to provide a method of treating burn victims.

It is still another object of the present invention to employ the principles of genetic engineering to modify human hemoglobins to improve oxygen delivery for the treatment of solid tumors by radiation therapy.

The above objects and other objects, aims, advantages and goals are satisfied by the present invention.

The present invention concerns a substantially pure polynucleotide coding for an alpha and/or beta human globin, the globin when part of a hemoglobin molecule confering lower oxygen affinity than normal hemoglobin to result in a mutant hemoglobin, the mutant hemoglobin to have an oxygen affinity measured for stripped hemoglobin characterized by a $P_{50}$ of 30 torr to 3 atmospheres (2,280 torr) and/or by a Hill coefficient between 2.5 and 1.0.

The invention also concerns a replicable recombinant DNA cloning vehicle having an insert comprising the aforementioned polynucleotide. The invention further relates to a cell that is transfected, infected or injected with a recombinant cloning vehicle as described above.

The invention also concerns a peptide encoded by the aforementioned polynucleotide and produced by recombinant DNA technology, a DNA coding for such peptide, an expression vector comprising such DNA and a host organism transformed with such expression vector.

The present invention also relates to a method of increasing tissue oxygenation in a warm blooded animal patient, e.g., human patient, comprising administering to the patient a therapeutically effective amount of a substantially pure mutant alpha or beta hemoglobin (e.g., human hemoglobin), the hemoglobin having a lower oxygen affinity than normal hemoglobin and the mutant hemoglobin having an oxygen affinity measured for stripped hemoglobin characterized by a $P_{50}$ of 30 torr to 3 atmospheres (2,280 torr) and/or by a Hill coefficient between 2.5 and 1.0.

Still further, the present invention is directed to a method of replacing hemoglobin in the bloodstream of a warm blooded animal patient, e.g., a human patient, comprising administering to the patient an effective amount of a substantially pure mutant alpha or beta hemoglobin, the mutant hemoglobin having a lower oxygen affinity than normal hemoglobin and the mutant hemoglobin having an oxygen affinity measured for stripped hemoglobin characterized by a $P_{50}$ of 30 torr to 3 atmospheres (2,280 torr) and by a Hill coefficient between 2 5 and 1.0.

The present invention is also directed to a method of treating a warm blooded animal, e.g., a human, patient exposed to a burn comprising administering to the patient a therapeutically effective amount of a substantially pure mutant alpha or beta hemoglobin, the mutant hemoglobin having a lower oxygen affinity than normal hemoglobin and the mutant hemoglobin having an oxygen affinity measured for stripped hemoglobin characterized by a $P_{50}$ of 30 torr to 3 atmospheres and/or by a Hill coefficient between 2.5 and 1.0.

| DEFINITIONS | |
|---|---|
| Amino Axid | 3-letter code |
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG may be translated in three reading frames or phases, each of which affords a different amino acid sequence

```
GCT GGT TGT AAG   - Ala—Gly—Cys—Lys
G CTG GTT GTA AG  - Leu—Val—Val
GC TGG TTG TAA G  - Trp—Leu-(STOP).
```

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of the organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

cDNA Expression Vector—A procaryotic cloning vehicle which also contains sequences of nucleotides that facilitate expression of cDNA sequences in eucaryotic cells. These nucleotides include sequences that function as eucaryotic promoters, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referred to herein concerns the microinjection (use of a small syringe) of DNA into a cell.

Oxygenation Dissociation Curve—Graph showing the relationship of oxygen bound to hemoglobin and the ambient partial pressure of oxygen; usually expressed as percent saturation of hemoglobin versus the partial pressure of oxygen in torr (mm Hg).

$PO_2$—Ambient partial pressure of oxygen usually in torr (1 atmosphere equals 760 torr).

$P_{50}$—The partial pressure of oxygen ($PO_2$) which corresponds to half saturation of the hemoglobin oxygen binding sites.

n—Hill coefficient (the Hill coefficient for normal hemoglobin is 2.8 to 3.0).

Y—Fractional saturation of hemoglobin with oxygen.

Hill Equation—A mathematical relationship used to parameterize the oxygen dissociation curve. The Hill equation is as follows:

$$\text{Log} \frac{Y}{1-Y} = n \, \text{Log} \left( \frac{PO_2}{P_{50}} \right).$$

After mathematically fitting the Hill equation to the observed oxygen dissociation curve the characteristics of the particular curve can be described by the values of $P_{50}$ and n.

Bohr Effect—The decrease in hemoglobin oxygen affinity at lower (more acidic) pH.

Root Effect—An extreme Bohr effect observed in some hemoglobins of some fish. At acidic pH, circa 6.5, $P_{50}$ may reach several atmospheres.

Stroma-free Hemoglobin—Hemoglobin in solution isolated from the red blood cell and red blood cell membrane fragments.

Stripped Hemoglobin—Hemoglobin in solution free of the inorganic phosphates which modulate oxygen affinity (i.e., the 2,3-diphosphoglycerate normally bound to hemoglobin within the red blood cell). Stripped hemoglobin has a pH of generally 10 mmHg.

Cross-linked Hemoglobin—Hemoglobin modified by covalent bond cross-linkage between one or more of the alpha or beta globins. A technique used to increase the stability of the hemoglobin alpha-2 beta-2 tetrameric structure.

BRIEF DESCRIPTION OF THE DRAWINGS

For the purpose of illustrating the invention there is shown in the drawings forms which are presently preferred. It is to be understood, however, that the present invention is not limited to the precise arrangements and instrumentalities depicted in the drawings.

DETAILED DESCRIPTION OF THE INVENTION

Figure 1:
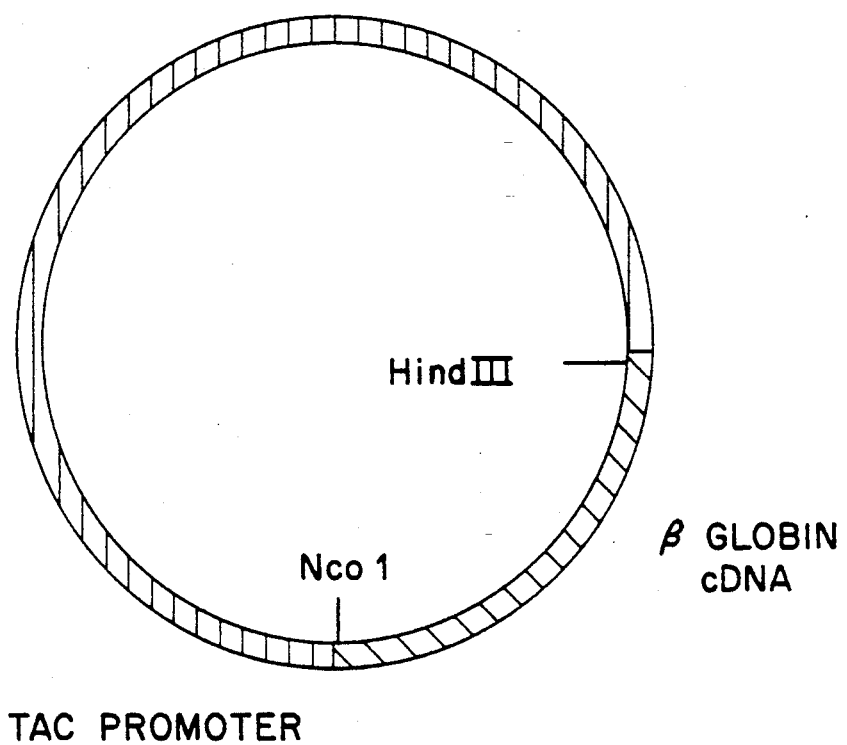
FIG. 1 is a schematic diagram depicting the cloning of human beta globin cDNA in *E. coli* expression vectors.

Normal human beta and alpha globin have the following amino acid sequences:

| beta | | | alpha | | |
|---|---|---|---|---|---|
| 1 Val | 65 Lys | 107 Gly | 1 Val | 60 Lys | 102 Ser |
| 2 His | 66 Lys | 108 Asn | 2 Leu | 61 Lys | 103 His |
| 3 Leu | 67 Val | 109 Val | 3 Ser | 62 Val | 104 Cys |
| 4 Thr | 68 Leu | 110 Leu | 4 Pro | 63 Ala | 105 Leu |
| 5 Pro | 69 Gly | 111 Val | 5 Ala | 64 Asp | 106 Leu |
| 6 Glu | 70 Ala | 112 Cys | 6 Asp | 65 Ala | 107 Val |
| 7 Glu | 71 Phe | 113 Val | 7 Lys | 66 Leu | 108 Thr |
| 8 Lys | 72 Ser | 114 Leu | 8 Thr | 67 Thr | 109 Leu |
| 9 Ser | 73 Asp | 115 Ala | 9 Asn | 68 Asn | 110 Ala |
| 10 Ala | 74 Gly | 116 His | 10 Val | 69 Ala | 111 Ala |
| 11 Val | 75 Leu | 117 His | 11 Lys | 70 Val | 112 His |
| 12 Thr | 76 Ala | 118 Phe | 12 Ala | 71 Ala | 113 Leu |
| 13 Ala | 77 His | 119 Gly | 13 Ala | 72 His | 114 Pro |
| 14 Leu | 78 Leu | 120 Lys | 14 Trp | 73 Val | 115 Ala |
| 15 Trp | 79 Asp | 121 Glu | 15 Gly | 74 Asp | 116 Glu |
| 16 Gly | 80 Asn | 122 Phe | 16 Lys | 75 Asp | 117 Phe |
| 17 Lys | 81 Leu | 123 Thr | 17 Val | 76 Met | 118 Thr |
| 18 Val | 82 Lys | 124 Pro | 18 Gly | 77 Pro | 119 Pro |
| 19 Asn | 83 Gly | 125 Pro | 19 Ala | 78 Asn | 120 Ala |
| 20 Val | 84 Thr | 126 Val | 20 His | 79 Ala | 121 Val |
| 21 Asp | 85 Phe | 127 Gln | 21 Ala | 80 Leu | 122 His |
| 22 Glu | 86 Ala | 128 Ala | 22 Gly | 81 Ser | 123 Ala |
| 23 Val | 87 Thr | 129 Ala | 23 Glu | 82 Ala | 124 Ser |
| 24 Gly | 88 Leu | 130 Tyr | 24 Tyr | 83 Leu | 125 Leu |
| 25 Gly | 89 Ser | 131 Gln | 25 Gly | 84 Ser | 126 Asp |
| 26 Glu | 90 Glu | 132 Lys | 26 Ala | 85 Asp | 127 Lys |
| 27 Ala | 91 Leu | 133 Val | 27 Glu | 86 Leu | 128 Phe |
| 28 Leu | 92 His | 134 Val | 28 Ala | 87 His | 129 Leu |
| 29 Gly | 93 Cys | 135 Ala | 29 Leu | 88 Ala | 130 Ala |
| 30 Arg | 94 Asp | 136 Gly | 30 Glu | 89 His | 131 Ser |
| 31 Leu | 95 Lys | 137 Val | 31 Arg | 90 Lys | 132 Val |
| 32 Leu | 96 Leu | 138 Ala | 32 Met | 91 Leu | 133 Ser |
| 33 Val | 97 His | 139 Asn | 33 Phe | 92 Arg | 134 Thr |
| 34 Val | 98 Val | 140 Ala | 34 Leu | 93 Val | 135 Val |
| 35 Tyr | 99 Asp | 141 Leu | 35 Ser | 94 Asp | 136 Leu |
| 36 Pro | 100 Pro | 142 Ala | 36 Phe | 95 Pro | 137 Thr |
| 37 Trp | 101 Glu | 143 His | 37 Pro | 96 Val | 138 Ser |
| 38 Thr | 102 Asn | 144 Lys | 38 Thr | 97 Asn | 139 Lys |
| 39 Gln | 103 Phe | 145 Tyr | 39 Thr | 98 Phe | 140 Tyr |
| 40 Arg | 104 Arg | 146 His | 40 Lys | 99 Lys | 141 Arg |
| 41 Phe | 105 Leu | | 41 Thr | 100 Leu | |
| 42 Phe | 106 Leu | | 42 Tyr | 101 Leu | |
| 43 Glu | | | 43 Phe | | |
| 44 Ser | | | 44 Pro | | |
| 45 Phe | | | 45 His | | |
| 46 Gly | | | 46 Phe | | |
| 47 Asp | | | 47 Asp | | |
| 48 Leu | | | 48 Leu | | |
| 49 Ser | | | 49 Ser | | |
| 50 Thr | | | 50 His | | |
| 51 Pro | | | 51 Gly | | |
| 52 Asp | | | 52 Ser | | |
| 53 Ala | | | 53 Ala | | |
| 54 Val | | | 54 Gln | | |
| 55 Met | | | 55 Val | | |
| 56 Gly | | | 56 Lys | | |
| 57 Asn | | | 57 Gly | | |
| 58 Pro | | | 58 His | | |
| 59 Lys | | | 59 Gly | | |

| beta | alpha |
|---|---|
| 60 Val | |
| 61 Lys | |
| 62 Ala | |
| 63 His | |
| 64 Gly | |

The present invention concerns a substantially pure polynucleotide coding for a mutant alpha or particularly, beta, human globin. It is preferred to make substitutions at human beta positions 90, 102, 108 and combinations thereof.

Preferred specific human beta mutations according to the invention include the following:
(1) amino acid 90 glutamine→lysine (hemoglobin Agenogi)
(2) amino acid 90 glutamine→glycine
(3) amino acid 108 asparagine→aspartic acid (hemoglobin Yoshizuka)
(4) amino acid 102 asparagine→threonine (hemoglobin Kansas)
(5) amino acid 102 asparagine→serine (hemoglobin Beth Israel)
(6) amino acid 90 glutamic acid→valine
   amino acid 91 lucine→methionine
   amino acid 93 cystine→serine
   amino acid 94 aspartic→glutamic acid (changes amino acid 86→100 from human beta to trout IV beta)

The purpose of mutant (6) above is to produce a mutant hemoglobin with a Root effect, since it is known that trout hemoglobin IV has a Root effect.

A preferred alpha mutation would be Asp to Asn at position 94 (hemoglobin Titusville).

The present invention provides the following uses:
a) Blood replacement stroma-free hemoglobin. Hemoglobin with decreased oxygen binding affinity would overcome one of the difficulties associated with using stroma-(red cells) free hemoglobin as a blood substitute, i.e., an increase in oxygen binding in the absence of red blood cell 2,3-DPG.
b) To improve tissue oxygenation in disease states associated with compromised oxygen delivery to tissue including myocardial infarction, stroke, small vessel disease such as diabetes, etc.
c) To overcome the problems of hypoxic tumor cells in radiation therapy.
d) Treatment of normal tissue radiation reactions resulting from vascular compromise.

The present invention serves to deliver more oxygen to tumor cells containing hypoxic cells and normal cells containing hypoxic cells due to damage by physical or chemical means, e.g., burns, exposure to chemicals, physical injuries or ionizing radiation.

The optimum values for $P_{50}$ and the Hill coefficient depend on a number of factors. The two are not independent, so that a low value of the Hill coefficient would help compensate for a low value of the $P_{50}$. The following Table recites non-limiting values for three different applications, namely, (1) blood replacement, (2) the treatment of vascular diseases, i.e., heart attack, stroke, diabetes, normal tissue vascular insufficiencies, etc., and for (3) radiation therapy. One set of values is given for hemoglobins which do not have a Root effect. For hemoglobins which have a Root effect, two sets of values are given, one set for the neutral pH at which loading would take place and one set for the acidic pH at which unloading would take place. A Root effect hemoglobin would probably not be particularly useful for blood replacement.

TABLE

| | Non-Root Effect Mutant Hemoglobins | | Root Effect-Mutant Hemoglobins | | | |
|---|---|---|---|---|---|---|
| | | | Neutral pH (loading) | | Acid pH (unloading) | |
| Blood Replacement | $P_{50}$ | 30–50 torr | | | | |
| | n | 3.0–2.0 | | | | |
| Vascular Disease | $P_{50}$ | 50–350 torr | $P_{50}$ | 25–150 torr | $P_{50}$ | >50 torr |
| | n | 3.0–1.0 | n | 3.0–2.0 | n | 3.0–1.0 |
| Radiation Therapy | $P_{50}$ | 75 torr - 3 ATA | $P_{50}$ | 25–350 torr | $P_{50}$ | 75 torr - 3 ATA |
| | n | 2.5–1.0 | n | 3.0–1.0 | n | 2.5–1.0 | n = Hill coefficient
Note:
Stripped human hemoglobin
$P_{50}$ 10 torr
n = 2.8–3.0
Human hemoglobin in red blood cell
$P_{50}$ 25 torr
n = 2.8–3.0

The mutant hemoglobin molecules according to the invention can be administered intravenously. They may be formulated in several ways, including, as stroma-free hemoglobin, as cross-linked stroma-free hemoglobin, contained in natural red blood cells, or contained in artificial red blood cells such as liposomes.

Sufficient hemoglobin would be administered intravenously to provide concentrations of from 2 to 12 gm % within the vascular system. For a human adult, this would correspond to a total dose of between 100 and 800 gm hemoglobin.

However, it may be necessary to deviate from the dosages mentioned and, in particular, to do so as a function of the nature and body weight of the subject to be treated, the nature and severity of the illness, the nature of the preparation and the administration, and the time or interval over which the administration takes place.

Thus, it can suffice in some cases to manage with less than the abovementioned amount of hemoglobin while in other cases the abovementioned amount of hemoglobin must be exceeded. The particular required optimum dosage can easily be decided by anyone skilled in the art on the basis of their expert knowledge.

FIG. 1 depicts the cloning of human beta globin cDNA in *E. coli* expression vectors (M13 and pProk-1). The human beta globin cDNA (Ncol-HindIII) was cloned under the control of the tac promoter into two different *E. coli* expression vectors. To facilitate the synthesis of single-stranded DNA for oligonucleotide mutagenesis, the beta cDNA was cloned into an M13 expression vector (mptac 18, Burroughs-Wellcome Laboratories, Langley Court, Bahenham, Kent BR3

EB5 England). The beta globin cDNA was also cloned into a conventional *E. coli* expression vector, pProk-1.

Figure 2:
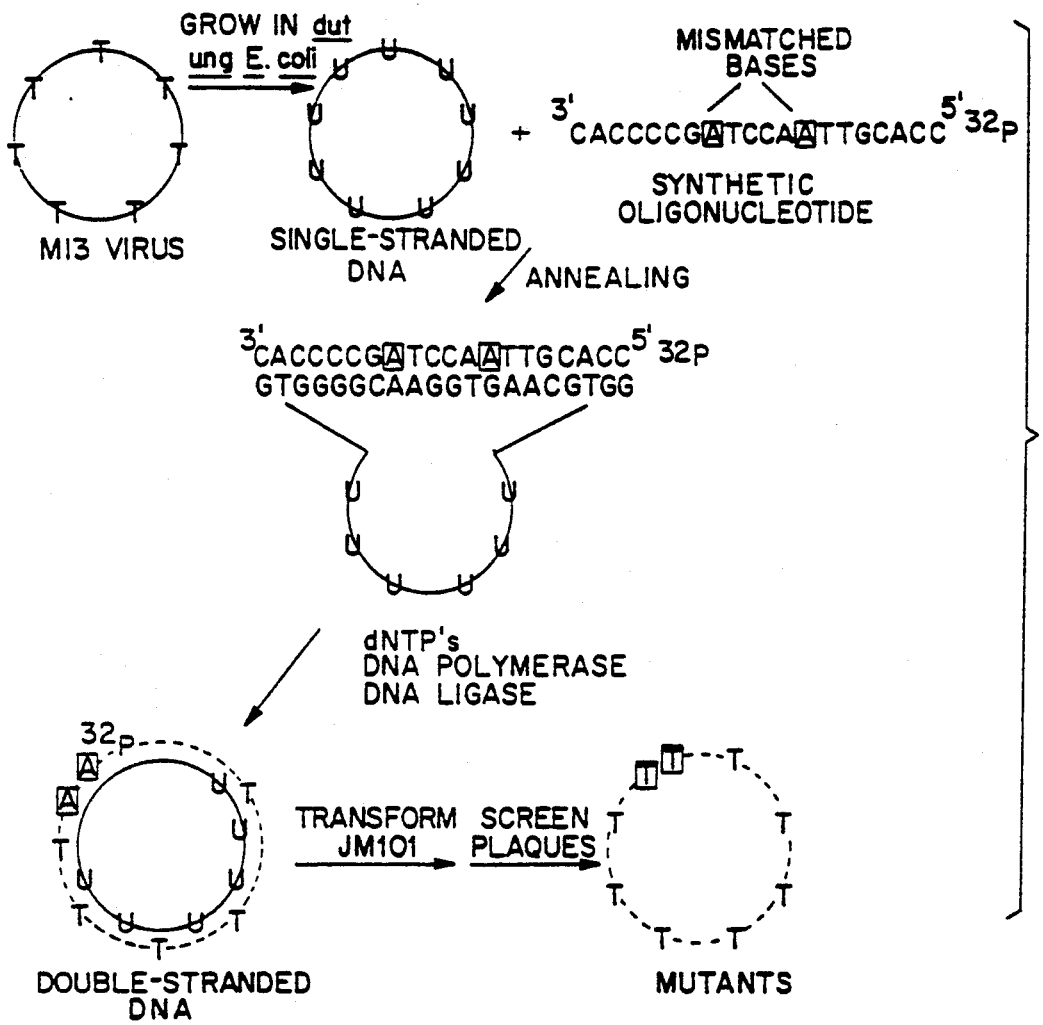
FIG. 2 is a schematic diagram depicting a technique of oligonucleotide-directed site-specific mutagenesis.

FIG. 2 depicts a technique of oligonucleotide-directed site-specific mutagenesis. Mutations in the human β globin gene were made by site-directed mutagenesis with specific oligonucleotides. The procedure followed was based on that of Kunkel, T.A., Roberts, J.D., Zakour, R., (1987), "Rapid and Efficient Site-Specific Mutagenesis Without Phenotypic Expression", *Meth Enzymol.* 154:367-382 and Zoller, M.J. and Smith M., (1983), "Oligonucleotide-directed Mutagenesis of DNA Fragments Cloned into M13 Vectors", *Meth Enzymol,* 100:468-500. All mutations were sequenced by the dideoxy DNA sequencing method.

Figure 3:
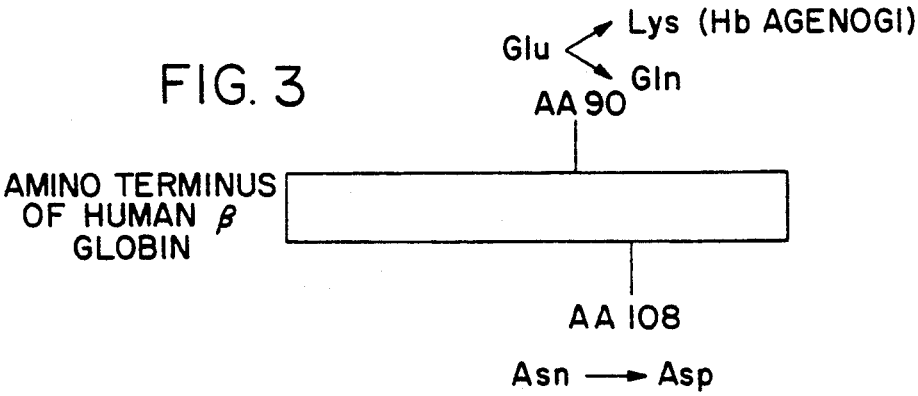
FIG. 3 is a schematic diagram depicting amino acid substitutions at positions 90 and 108 of human beta globin.

FIG. 3 depicts low affinity mutants of human beta globin constructed by site-specific mutagenesis. Single amino acid substitutions were made at amino acid 90 and amino acid 108. Two different oligonucleotides were used; the oligonucleotide for the mutations at amino acid 90 was a mixed oligonucleotide. M13 single-stranded DNA was used as the template for the mutagenesis.

Figure 4:
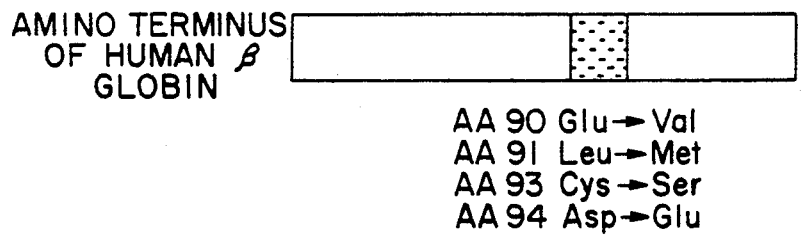
FIG. 4 is a schematic diagram depicting amino acid substitutions at positions 90, 91, 93 and 94 of human beta globin to construct a human-trout IV hybrid beta globin chain.

FIG. 4 depicts a human trout-IV hybrid beta-globin chain synthesized by oligonucleotide-directed mutagenesis using M13 single-stranded DNA as a template. Four amino acid substitutions were made by introducing single base pair mismatches in the oligonucleotide. This region of the trout beta globin protein may impart low oxygen affinity on the human beta chain.

Figure 5:
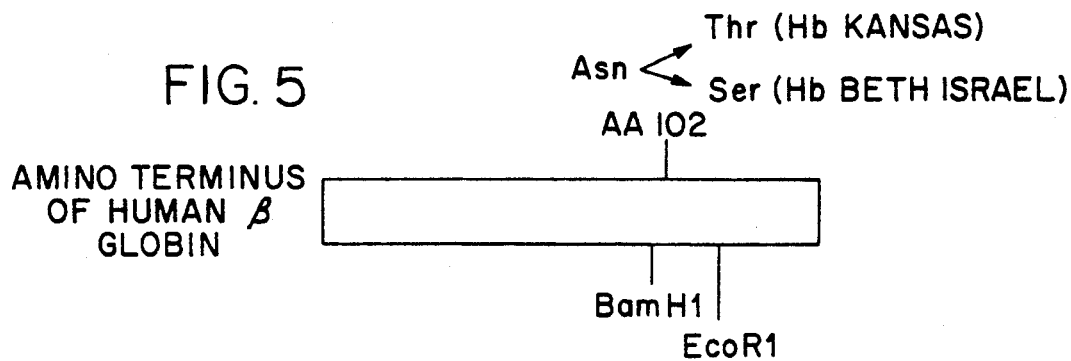
FIG. 5 is a schematic diagram depicting amino acid substitutions at position 102 of human beta globin to produce Hb Kansas and Hb Beth Israel.

FIG. 5 depicts low oxygen affinity mutants of human beta globin constructed by oligonucleotide insertion mutagenesis. Two amino acid substitutions were introduced at amino acid 102 by oligonucleotide insertion mutagenesis in a double-stranded expression vector, pProk-1. Two complementary oligonucleotides were synthesized in the restriction sites, BamH1 and EcoR1 at the ends. These were annealed and this fragment was exchanged for the corresponding normal BamH1-EcoR1 fragment of the human beta globin gene.

The invention will now be described with reference to the following non-limiting examples.

EXAMPLES

Reagents

Oligonucleotides were synthesized on an Applied Biosystems (Forster City, Calif.) DNA Synthesizer model 380B. Restriction enzymes were obtained from New England Biolabs (Beverly, Mass.) Sequenase and the Sequenase DNA sequencing kit were obtained from United States Biochemicals (Cleveland, Ohio).

Plasmids and *E. coli* Strains

The normal human beta globin cDNA was obtained from the University of Wisconsin (Madison, Wis.). pPROK-1 was obtained from Clontech (Palo Alto, Calif.). mptac18 was obtained from The Wellcome Research Laboratories, England. *E. coli* strain CJ236 was obtained from Yale University, New Haven, Conn.

EXAMPLE 1

Insertional Mutagenesis of the Beta Globin cDNA

The normal human beta globin cDNA was cut with BamH1 and EcoR1, which cut within the protein coding region and includes AA 102. Two complementary oligonucleotides, each 67 bases in length and bearing BamH1 and EcoR1 ends were synthesized. The contain a mixture of mutations which changes the codon at amino acid (AA) 102 from AAC (Asn) to AGC (Ser, Hb Beth Israel) or ACC (Thr, Hb Kans.). The sequence of the oligonucleotides is

The oligonucleotides were purified, kinased, annealed together and then ligated into the BamH1-EcoR1 cut beta cDNA. The presence of the inserted oligonucleotides was confirmed by the addition of a new AvrII site and the lack of Bstx1 site when compared to the normal beta cDNA. The inserted DNA was sequenced using the dideoxy sequencing method (Sequenase kit) on double-stranded plasmid DNA through both cloning sites.

EXAMPLE 2

Subcloning into pPROK-1

The Nco1-HindIII fragment of the mutated beta globin cDNAs, containing the complete protein coding region for the beta globin chain, were subcloned into the Nco1-HindIII sites of plasmid pPROK-1, and *E. coli* expression vector which uses a tac promoter.

EXAMPLE 3

Site-specific mutagenesis of beta globin cDNA

To facilitate cloning of the Nco1-HindIII fragment of the normal beta globin cDNA into mptac18, an Nco1 site was introduced into mptac18 by site-specific mutagenesis. mptac18 is an *E. coli* bacteriophage expression vector which uses the tac promoter and produces single-stranded DNA suitable for site-specific mutagenesis. A 30-mer which introduces this mutation in the polylinker region of mptac18 was synthesized and used in the mutagenesis reaction. Mutagenesis was performed using the strains developed by Kunkel, supra, and the procedure of Zoller and Smith, supra. This is outlined in FIG. 2. Mutants were screened by the presence of a new Nco1 site in M13 RF.

The Nco1-HindIII fragment of the beta globin cDNA was subcloned into the mutated mptac18 vector. The presence of the insert was confirmed by dideoxy sequencing (Sequenase kit) of the single-stranded DNA. Site-directed mutagenesis was performed using the following oligonucleotides.

This changes the codon at AA 90 from GAG (Glu) to CAG (Gln) and AAG (Lys, Hb Agenogi).

This changes the codon at AA 108 from AAC (Asn) to GAC (Asp).

3) to change AA 86-100 of human beta chain to trout IV beta chain
5' CAC GTG CAG CTT CTC ACT GTG CAT CAC ACT CAG TGT GGC This changes these codons:

AA 90 GAG (Glu)⟶GTG (Val)
AA 91 TTG (Leu)⟶ATG (Met)
AA 93 TGT (Lys)⟶AGT (Ser)
AA 94 GAC (Asp)⟶GAG (Glu).

Mutagenesis was performed using the *E. coli* strains developed by Kunkel supra and the procedure developed by Zoller and Smith supra. The sequence of the mutants was determined by dideoxy DNA sequencing of the single-stranded DNA template (Sequenase kit).

EXAMPLE 4

Expression of beta globin clones

Alpha and beta globin clones have been expressed successfully in a number of different ways. Simply, they can be expressed in either prokaryotes, such as *E. coli* of eukaryotes, such as mammalian cells.

Expression in *E. coli* requires that the gene be cloned behind an *E. coli* transcription promoter, that a Shine-Dalgarno sequence (ribosome binding sites) be present in the mRNA and that the protein be stable in order to facilitate purification. Alpha and beta globin chains have been expressed using a lambda cII promoter (Nagai, K., Perutz, M.F. and Poyart, C., (1985), "Oxygen Binding Properties of Human Mutant Hemoglobins Synthesized in *Escherichia coli.*", *Proc. Natl. Acad. Sci. USA,* 82:7252–7255; Luisi, B.F. and Nagai, K., (1986), "Crystallographic Analysis of Mutant Human Hemoglobins Made in *Escherichia coli.*", *Nature,* 320:555–556). The chains were purified and then reconstituted with heme. Other promoters can be used for expression including the tac promoter (Brinigar, W.S., Chao, T.L., Debouck, C., Gorman, J., Gorman, J.W., Lichenstein, H., O'Donnell, J.K., Sutton, J.A. and Young, J.F., (1988), "Expression of Human Beta-Globin cDNA in *E. coli.* Streptomyces and Yeast", Abstract from the Symposium on Oxygen Binding Heme Proteins: Structure, Dynamics, Function and Genetics, Oct. 9–13, 1988).

Two of applicants' mutants, Hb Kansas and Hb Beth Israel, are cloned into pPROK-1, and *E. coli* expression vector which uses the tac promoter. Expression of the mutant globin chains can be induced by IPTG, the protein purified and then re-associated with alpha chain and heme. The other mutants described hereinabove are cloned into a single-stranded expression vector under the control of a tac promoter (mptac18). This vector has been used to express the reverse transcriptase gene from HIV (Larder, B., Pinfoy, D., Powell, D. and Darby, G., (1987), "AIDS Virus Reverse Transcriptase Defined by High Level Expression in *Escherichia coli*", *EMBO J,* 6:3133–3137). It is also possible to express both chains simultaneously, as has been demonstrated in Hela cells (Stacey, D.W. and Allfrey, V.G., (1976), "Microinjection Studies of Duck Globin Messenger RNA Translation in Human and Avian Cells", *Cell,* 9:725–732). This would obviate the need for re-association after purification.

In eukaryotes, globins have been expressed in several different species and cell types. Beta globin genes have been successfully expressed in yeast (Brinigar, et al, 1988, supra) as well as in several mammalian systems. Beta globin genes have been expressed in vivo in hematopoietic stem cells of mice (Karlsson, S., Van Doren, K., Schweiger, S.G., Nienhuis, A.N. and Gluzman, Y., (1986), "Stable Gene Transfer and Tissue-Specific Expression of a Human Globin Gene Using Adenovial Vectors", *EMBO J,* 5:2377–2385) in transgenic mice (Chada, K., Magram, J., Raphael, K. Radice, G., Lacy, E. and Costantini, F., (1985), "Specific Expression of a Foreign Beta-Globin Gene in Erythroid Cells of Transgenic Mice", *Nature.* 314:377–380; Soriano, P., Cone R.D., Mulligan R.-C. and Jaenisch, R., (1986) "Tissue-Specific and Ectopic Expression of Genes Introduced into Transgenic Mice by Retroviruses", *Science,* 234:1409–1413 and Townes, T.M., Lingrel, J.B., Chen, H.-Y., Brinster, R.L. and Palmiter, R.D., (1985), "Erythroid-Specific Expression of Human Beta-Globin Genes in Transgenic Mice, *EMBO J,* 4:1715–1723) and in vitro in mouse erythroleukemia cells (Charnay, P., Treisman, R., Mellon, P., Chao, M., Axel, R. and Maniatis, T., (1984), "Differences in Human Alpha and Beta Globin Gene Expression in Mouse Erythroleukemia Cells: The Role of Intragenic Sequences", *Cell.* 38:251). Again, in these or analogous systems, one or both chains could be expressed (Stacey and Allfrey, 1976, supra).

It will be appreciated that the instant specification and claims are set forth by way of illustration and not limitation, and that various modifications and changes may be made without departing from the spirit and scope of the present invention.

What is claimed is:

1. A substantially pure polynucleotide coding for an alpha and/or beta globin, said globin when part of a hemoglobin molecule confering lower oxygen affinity than normal hemoglobin to result in a mutant hemoglobin, said mutant hemoglobin having an oxygen affinity measured for stripped hemoglobin characterized by a $P_{50}$ of 50 torr to 3 atmospheres and/or by a Hill coefficient between 2.5 and 1.0.

2. A substantially pure polynucleotide coding for a mutant alpha and/or beta human globin according to claim 1.

3. A polynucleotide according to claim 1 produced by recombinant DNA technology.

4. The substantially pure polynucleotide according to claim 1, wherein the polynucleotide codes for a mutant globin selected from the group consisting of trout IV, Kansas, Beth Israel, Yoshizuka, Titusville and Agenogi.

5. The substantially pure polynucleotide according to claim 4, produced by recombinant DNA technology.

6. The substantially pure polynucleotide according to claim 5, wherein the polynucleotide codes for a trout IV beta globin with replacement of human beta amino acids 86–100 for trout IV beta amino acids 86–100.

7. The substantially pure polynucleotide according to claim 1, wherein the polynucleotide codes for a Root effect hemoglobin.

8. The substantially pure polynucleotide according to claim 1, wherein the $P_{50}$ is 50 to 350 torr and the Hill coefficient is 3 to 1.

9. The substantially pure polynucleotide according to claim 1, wherein the $P_{50}$ is 50 to 150 torr and the Hill coefficient is 3 to 2.

10. The substantially pure polynucleotide according to claim 1, wherein the $P_{50}$ is greater than 50 torr and the Hill coefficient is 3 to 1.

11. The substantially pure polynucleotide according to claim 1, wherein the $P_{50}$ is 75 torr to 3 atmospheres and the Hill coefficient is 2.5 to 1.

12. The substantially pure polynucleotide according to claim 1, wherein the polynucleotide comprises the following beta globin sequence:

```
                                                      C
AATTCTTTGCCAAAGTGATGCGCCAGCACACAGACCAGCACGTTGCCTAGGAGCCTGAAGGTCTCAG
5'——|——|——|——|——|——|——|——|——|——|——|——|——|——|——|——|——|——|——|——|——|——
``` changing the codon at amino acid position 102 from AAC (Asn) to AGC (Ser)

13. The substantially pure polynucleotide according to claim 1, wherein the polynucleotide comprises the following beta globin sequence:

```
              G
5' C ACA GTG CAG CTT ACT CAG TGT G
``` changing the codon at amino acid position 90 from GAG (Glu) to CAG (Gln)

14. The substantially pure polynucleotide according to claim 1, wherein the polynucleotide comprises the following beta globin sequence:

```
at AA 108  5' ACA GAC CAG CAC GTC GCC CAG GAG CCT -3'
``` changing the codon at amino acid position 108 from AAC (Asn) to GAC (Asp)

15. The substantially pure polynucleotide according to claim 1, wherein the polynucleotide comprises the following beta globin sequence:

```
5' CAC GTG CAG CTT CTC ACT GTG CAT CAC ACT CAG TGT GGC
``` changing the following codons:
   amino acid position 90 from GAG (Glu) to GTG (Val)
   amino acid position 91 from TTG (Leu) to ATG (Met)
   amino acid position 93 from TGT (Lys) to AGT (Ser)
   amino acid position 94 from GAC (Asp) to GAG (Glu).

16. A replicable recombinant DNA cloning vehicle having an insert comprising the polynucleotide according to claim 1.

17. A cell that is transfected, infected or injected with a recombinant cloning vehicle according to claim 16.

* * * * *